United States Patent
Doppiu et al.

(10) Patent No.: US 9,339,804 B2
(45) Date of Patent: May 17, 2016

(54) METHOD FOR PREPARATION OF A RUTHENIUM INDENYLIDENE COMPLEX

(71) Applicant: UMICORE AG & CO. KG, Hanau-Wolfgang (DE)

(72) Inventors: Angelino Doppiu, Seligenstadt (DE);
Beate Heil, Bischofsheim (DE);
Andreas Rivas-Nass, Schriesheim (DE);
Eileen Woerner, Nidderau (DE); Ralf Karch, Kleinostheim (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 14/410,160

(22) PCT Filed: Jun. 25, 2013

(86) PCT No.: PCT/EP2013/063208
§ 371 (c)(1),
(2) Date: Dec. 22, 2014

(87) PCT Pub. No.: WO2014/001291
PCT Pub. Date: Jan. 3, 2014

(65) Prior Publication Data
US 2015/0190795 A1    Jul. 9, 2015

(30) Foreign Application Priority Data

Jun. 26, 2012  (EP) ..................................... 12173596

(51) Int. Cl.
*B01J 31/22*    (2006.01)
*C07F 15/00*    (2006.01)
*B01J 37/03*    (2006.01)
*B01J 37/06*    (2006.01)

(52) U.S. Cl.
CPC ............ *B01J 31/2265* (2013.01); *B01J 37/031* (2013.01); *B01J 37/06* (2013.01); *C07F 15/0046* (2013.01); *B01J 2231/543* (2013.01); *B01J 2531/821* (2013.01)

(58) Field of Classification Search
CPC ...... B01J 31/2265; B01J 37/06; B01J 37/031; B01J 2531/821; B01J 2231/543; C07F 15/0046
See application file for complete search history.

(56) References Cited

U.S. PATENT DOCUMENTS 8,703,985 B2 * 4/2014 Winde ................ C07F 15/0046
556/136

FOREIGN PATENT DOCUMENTS

| EP | 2 280 033 A1 | 2/2011 |
| WO | 2010/037550 A1 | 4/2010 |

OTHER PUBLICATIONS

International Search Report for PCT/EP2013/063208, mailed Jul. 31, 2013.
Dorta, R., et al. "Cross Metathesis Allowing the Conversion of a Ruthenium Indenylidene Complex into Grubbs', Catalyst", *Adv. Synth. Catal.*, vol. 346 (2004), pp. 917-920.
Fürstner, A., et al., "Indenylidene Complexes of Ruthenium: Optimized Synthesis, Structure Eludication, and Performance as Catalysts for Olefin Metathesis—Application to the Synthesis of the ADE-Ring System of Nakadomarin A", *Chem. Eur. J.*, vol. 7, No. 22 (2001), pp. 4811-4820.
Fürstner, A., et al., "Total Synthesis and Structural Refinement of the Cyclic Tripyrrole Pigment Nonylprodigiosin", *J. Org. Chem.*, vol. 64 (1999), pp. 8275-8280.
Harlow, K.J., et al., "The First Co-Ordinatively Unsaturated Group 8 Allenylidene Complexes: Insights into Grubbs' vs. Dixneuf-Fürstner Olefin Metathesis Catalysts", *J. Chem. Soc., Dalton Trans.*, (1999), pp. 285-291.
Hurley, P.B., et al., "Synthetic Studies Toward Halichlorine: Complex Azaspirocycle Formation with Use of an NBS-Promoted Semipinacol Reaction", *J. Org. Chem.*, vol. 73 (2008), pp. 4131-4138.
Shaffer, E.A., et al., "Synthesis of Ruthenium Phenylindenylidene, Carbyne, Allenylidene and Vinylmethylidene Complexes from $(PPh_3)_{3-4}RuCl_2$: A Mechanistic and Structural Investigation", *Journal of Organometallic Chemistry*, vol. 692 (2007), pp. 5221-5233.
Schanz, H-J., et al., "Coordinatively Unsaturated 16-Electron Ruthenium Allenylidene Complexes: Synthetic, Structural, and Catalytic Studies", *Organometallics*, vol. 18 (1999), pp. 5187-5190.

* cited by examiner

*Primary Examiner* — Sudhakar Katakam
(74) *Attorney, Agent, or Firm* — Brinks Gilson & Lione

(57) ABSTRACT

The present invention is directed to a method for the preparation of ruthenium catalyst $(PCy_3)_2Cl_2Ru(phenylindenylidene)$ (Umicore catalyst "M1"). The method comprises a one-step reaction reacting the precursor compound $(PPh_3)_2Cl_2Ru(3-phenylindenylidene)$ with $PCy_3$ in a cyclic ether solvent (preferably THF) in concentrations in the range of 0.2 to 0.6 mol catalyst/l while simultaneously precipitating the product from the reaction mixture. A cyclic ether solvate product with high crystallinity and high purity is obtained.

10 Claims, 7 Drawing Sheets

METHOD FOR PREPARATION OF A RUTHENIUM INDENYLIDENE COMPLEX

This application is a National Stage application of International Application No. PCT/EP2013/063208, filed Jun. 25, 2013, which claims the benefit of European Application No. 12173596.3, filed Jun. 26, 2012.

The present invention relates to a ruthenium-carbene catalysts for olefin metathesis reactions, in particular to the preparation of a ruthenium indenylidene carbene catalyst of the formula $(PCy_3)_2Cl_2Ru$(3-phenylindenylidene) with the chemical name dichloro(3-phenyl-1H-inden-1-ylidene)bis(tricyclohexylphosphine)ruthenium(II). Furthermore, the invention is directed to a new crystalline form of said catalyst.

The catalyst product is commercially available as catalyst Umicore M1 and hereinafter designated with the abbreviations "Umicore M1" or "M1" for short. It is useful in a variety of olefin metathesis reactions and as precursor for the synthesis of other ruthenium carbene catalysts. The present invention provides a one-step method with simple product isolation. A highly crystalline material is obtained, which displays high purity and good thermal stability as well as very good stability towards atmospheric oxygen.

Olefin metathesis is a fundamental catalytic reaction and one of the most versatile ways to design new molecules by formation and rearrangement of carbon-carbon multiple bonds. The metathesis reactions not only provide significantly shortening synthetic pathways towards defined target molecules, but also give access to new applications not being feasible with the traditional means of organic chemistry. Various classes of metathesis reactions are known, such as, for example, ring-closing metathesis (RCM), ring-opening metathesis polymerization (ROMP) or cross metathesis (CM).

In the past years, metathesis has become a widely used method for the formation of carbon-carbon bonds in organic synthesis and polymer chemistry. The development of well-defined ruthenium-based carbene catalysts by Grubbs has led to a fast growth in the field of metathesis. More and more, metathesis reactions are applied and integrated in the synthesis design of organic compounds, leading to an increased usage of metathesis catalysts in industrial laboratories. This trend is about to continue in the forthcoming years.

One of the first catalyst showing high activity, low sensitivity against functional groups as well as sufficient stability, was Grubbs "first generation" catalyst $(PCy_3)_2Cl_2Ru=CHPh$, dichloro(benzylidene)bis(tricyclohexylphosphine)ruthenium(II). This catalyst is characterized by a penta-coordinated Ru(II) metal center bearing two phosphine ligands, two chloride ligands and a non-cyclic benzylidene group and has found broad acceptance in the organic synthesis community.

In the meantime, a complete range of different metathesis catalysts, each offering specific features and properties are available on the market from different vendors. Over the past years, a different class of metathesis catalysts, so-called Ruthenium indenylidene carbene catalysts have gained increased importance. These types of Ru-carbene catalysts contain the Ru atom in the formal oxidation state +II; they are predominantly penta-coordinated and comprise an indenylidene ring, wherein the carbene C-atom in the indenylidene moiety is part of a bicyclic, condensed ring system.

The present invention is directed to a preparation method for the Grubbs-1$^{st}$ generation type Ru-phenylindenylidene catalyst exhibiting the structure of Formula 1:

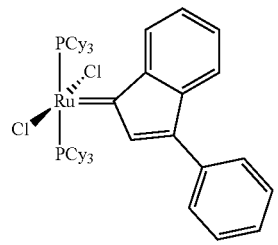

Formula 1

This catalyst, dichloro(3-phenyl-1H-inden-1-ylidene)bis-(tricyclohexylphosphine)-ruthenium(II) (CAS Nr.: 250220-36-1), was first published in 1999 by A. F. Hill et al. in *J. Chem. Soc., Dalton Trans.* 1999, 285-291. It was obtained by a ligand substitution reaction of dichloro(3-phenyl-1H-inden-1-ylidene)bis-(triphenylphosphine)ruthenium(II), $(PPh_3)_2Cl_2Ru$(3-phenylindenylidene) (CAS Nr.: 254972-46-8) with tricyclohexylphosphine $(PCy_3)$. The molecular formula of Umicore M1 is $C_{51}H_{76}Cl_2P_2Ru$.

The method of the present invention essentially is a one-step method, starting from the $PPh_3$-substituted Ru-complex, which is prepared in a separate reaction. The $PPh_3$-substituted Ru-indenylidene carbene complex is shown in Formula 1a:

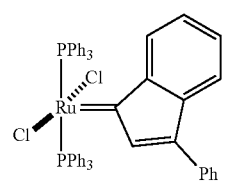

Formula 1a

The synthesis routes for the starting complex of Formula 1a are well known in the literature and will be outlined in the following.

Preparation of the Starting Complex (1a)

As described by Hill (ref to A. F. Hill et al., cited above) the starting material $(PPh_3)_2Cl_2Ru$(3-phenylindenylidene) is obtained by reacting di-chlorotris(triphenylphosphine)ruthenium(II), $[(PPh_3)_3Cl_2Ru]$ with 1,1-diphenyl-2-propyn-1-ol in THF at reflux for 2.5 hours. It was first believed that the reaction would provide the corresponding diphenylallenylidene complex $(PPh_3)_2Cl_2Ru=C=C=CPh_2$. However, it was found later by Fuerstner et al. that the structure of this complex was not an allenylidene, instead it was re-arranged to an phenylindenylidene (ref to Fuerstner et al, *J. Org. Chem.* 1999, 7, No. 64, 8275-8280). This complex $(PPh_3)_2Cl_2Ru$(3-phenylindenylidene) is itself not active in olefin metathesis reactions and the two triphenylphosphine ligands must be exchanged for tricyclohexylphosphine in order to achieve catalytic activity.

Recently, the synthesis of the starting complex $(PPh_3)_2Cl_2Ru$(3-phenylindenylidene) was investigated in greater detail by H.-J. Schanz et al. in *J. Organometal. Chemistry* 692, 5221-5233 (2007). The reaction of $(PPh_3)_{3-4}Cl_2Ru$ with 1,1-diphenyl-2-propyn-1-ol is conducted in refluxing THF for 1.5 hours to yield the starting complex; improved yields and high purity products are reported under acidic conditions. Schanz also reported that several undesired side products are generated if the reaction conditions are not carefully controlled. This preparation route is shown in equation 1.

Equation 1:

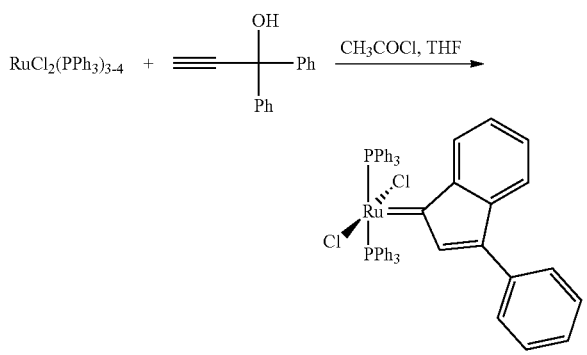

According to this reaction, the starting (PPh$_3$)$_2$Cl$_2$Ru(3-phenylindenylidene) complex is prepared separately and isolated as a solid material that is used as educt for the preparation method of the present invention (ref to Example 1).

Preparation of the Umicore M1 Catalyst

Generally, two different synthetic routes to the metathesis catalyst (PCy$_3$)$_2$Cl$_2$Ru(3-phenylindenylidene (Umicore M1 catalyst) are reported in the literature: These routes are summarized in equation 2.

Equation 2:

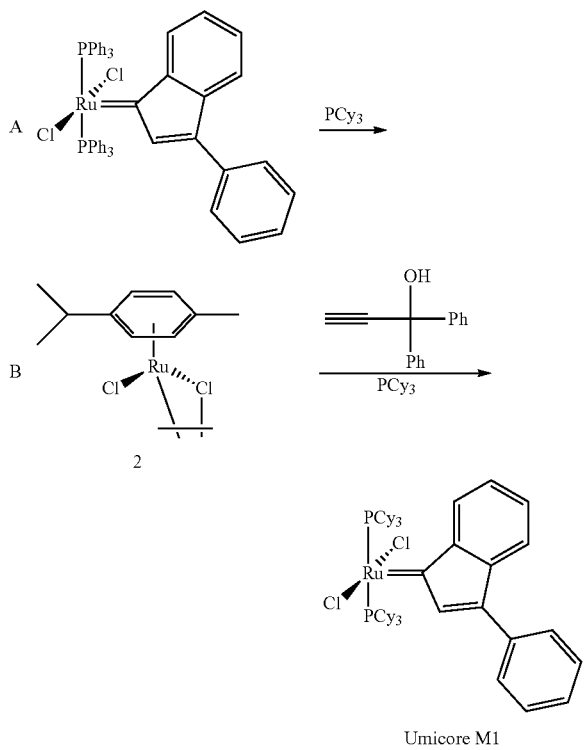

Umicore M1

The route B (ref to S. Nolan et al, *Organometallics*, 1999, 18, 5187-5190) affords a product of poor quality in very low yields. In fact, a mixture of diphenylallenylidene and phenylindenylidene species is obtained. The diphenylallenylidene complex (PCy$_3$)$_2$Cl$_2$Ru=C=C=CPh$_2$ displays lower catalytic activity compared to the phenylindenylidene complex. This route was evaluated by the present inventors without success and will be not considered here. The "ligand exchange route" A is broadly described in the literature and some variants thereof are known. These variants will be reported hereinafter.

According to Hill (cited above) the product is obtained by a one-step ligand substitution reaction of (PPh$_3$)$_2$Cl$_2$Ru(3-phenylindenylidene) with 2.7 equivalents of tricyclohexylphosphine in dichloromethane at room temperature for 0.5 hours with a concentration of c=0.015 mol/l of the starting Ru-complex. The product (PCy$_3$)$_2$Cl$_2$Ru(3-phenylindenylidene) is isolated as brick-red solid in 88% yield after evaporation of the solvent to dryness and trituration of the residue with methanol, followed by washing with methanol and hexane.

Fuerstner described an optimized preparation method, based on the one-step reaction of (PPh$_3$)$_2$Cl$_2$Ru(3-phenylindenylidene) with 3.1 equivalents tricyclohexylphosphine (PCy$_3$) in dichloromethane at room temperature for 2 hours in a concentration of c=0.043 mol/l (ref to Fuerstner et al, *Chem. Eur. J.* 2001, 7, No. 22, 4811-4820). The product is obtained as an orange powder in 80% yield (after evaporation to dryness and trituration and washing with hexane). Since the solvent is stripped off completely before isolation, this method is not suitable for industrial scale manufacturing.

Nolan et al. (*Adv. Synth. Catal.* 2004, 346, 917-920) described a one-pot, two-step synthesis of (PCy$_3$)$_2$Cl$_2$Ru(3-phenylindenylidene) by reaction of (PPh$_3$)$_3$RuCl$_2$ with 1,1-diphenyl-2-propyn-1-ol in refluxing THF, followed by a ligand exchange reaction of the resulting (PPh$_3$)$_2$Cl$_2$Ru(3-phenylindenylidene) complex with 2.7 equivalents PCy$_3$ in the same solvent by stirring overnight at room temperature with a concentration of c=0.031 mol/l. The complex is isolated as brick-red solid in 92% yields by evaporating the solvents and suspending the residues in diethylether. Thereafter the product is filtered and washed frequently with low boiling solvents such as diethylether and pentane to remove impurities. As this procedure is a one-pot, 2-step method, it generally yields a product in lower purity. As the intermediate (PPh$_3$)$_2$Cl$_2$Ru(3-phenylindenylidene) is not isolated but directly reacted with tricyclohexylphosphine, the amount of side products is quite high.

Dake et al. (*J. Org. Chem.*, 2008, 73 (11), 4131-4138) reported a one-step synthesis of (PCy$_3$)$_2$Cl$_2$Ru(3-phenylindenylidene) by reaction of (PPh$_3$)$_2$Cl$_2$Ru(3-phenylindenylidene) with 2.99 equivalents tricyclohexylphosphine in dichloromethane at room temperature for 2 hours in a concentration of c=0.022 mol/l. The product is obtained as an orange powder in 66% yield after evaporation to dryness and trituration for 12 hours with hexane. Since the solvent is stripped off completely before isolation, this method is not suitable for industrial scale manufacturing.

WO2010/037550A1 describes a one-pot, two-step synthesis of (PCy$_3$)$_2$Cl$_2$Ru(3-phenylindenylidene) by reaction of (PPh$_3$)$_3$RuCl$_2$ with 1,1-diphenyl-2-propyn-1-ol in dioxane at 90° C. in presence of an acid. The ligand exchange reaction between the resulting (PPh$_3$)$_2$Cl$_2$Ru(3-phenylindenylidene) complex and 2.33 equivalents PCy$_3$ is carried out with a concentration of c=0.12 mol/l at 90° C. for 10 min. The complex is isolated in 90% yield as orange solid by distilling off 60% of the solvent and then by filtration and washing with methanol. This synthesis is a one-pot, 2-step method, which yields a product in lower purity and/or lower crystallinity. This method is hereinafter cited as "Umicore Standard Method" and will be used for Comparative Experiments.

Afanasiev et al. (EP2280033A1) describes a one-pot, two-step synthesis of (PCy$_3$)$_2$Cl$_2$Ru(3-phenylindenylidene) by reaction of (PPh$_3$)$_3$RuCl$_2$ with 1,1-diphenyl-2-propyn-1-ol in refluxing THF. After removal of 50% of the THF by distillation, the ligand exchange reaction between the resulting (PPh$_3$)$_2$Cl$_2$Ru(3-phenylindenylidene) complex and 3.2 equivalents PCy$_3$ is carried out. Hereby, the mixture is stirred for 8 hours at room temperature with a concentration of c=0.039 mol/l. The complex is isolated in 95% yields by removing the solvent and suspending the residue in acetone at −40° C. for 10 hours, followed by filtration and washing with methanol, acetone and hexane. As with the method of Nolan before, this synthesis is a one-pot, two-step method, generally yielding a product in lower purity and lower crystallinity. The impurities (e.g. diphenylallenylidene species, dimeric compounds, mixed PPh$_3$/PCy$_3$ complexes, phosphine oxides etc) may lead to performance losses of the final catalyst product, such as lower activity, higher catalyst consumption and lower turn-over numbers (TON).

When referring to the one-step methods of preparation (i.e. the methods of Hill, Fuerstner and Dake), the phosphine ligand exchange reaction is conducted in chlorinated solvents (typically dichloromethane) at room temperature (i.e. 20 to 25° C.). After completion of the reaction, the solvent is evaporated to dryness and the product is washed with big amounts of low boiling solvents in order to wash out the phosphine impurities. In most cases, a high excess of tricyclohexylphosphine (in the range of 2.5 to 3.2 equivalents) is employed. This may lead to phosphine and phosphine oxide residues in the final product. Furthermore, as the currently known procedures do not comprise a specific purification step (other than washing the residual material with solvent) the impurities are not efficiently removed from the final product.

In summary, the currently known preparation methods (either one-step or two-step methods) for the (PCy$_3$)$_2$Cl$_2$Ru(3-phenylindenylidene) complex are lengthy, comprise long reaction times, yield a low purity product and are, due to the fact that the solvents are in most cases evaporated to dryness, not applicable to industrial production scale.

It was therefore an objective of the present invention to provide an improved method for preparation of the (PCy$_3$)$_2$Cl$_2$Ru(3-phenylindenylidene) complex (Umicore "M1" catalyst). The method should be straightforward and easily scalable; it should yield the M1 catalyst in high purity, high crystallinity and good yield, in particular a good space yield (i.e. amount of product per reactor volume). Furthermore, the method should be essentially based on a one-step method and should be applicable to industrial production scale.

This objective is reached by the method of the present invention.

The present invention is directed to a one-step method for preparation of the ruthenium indenylidene catalyst of Formula 1,

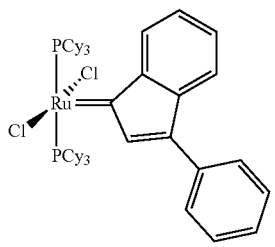

Formula 1 said method comprising
reacting (PPh$_3$)$_2$Cl$_2$Ru(3-phenylindenylidene) with tricyclohexylphosphine (PCy$_3$) in a reaction mixture having a concentration in the range of 0.2 to 0.6 mol catalyst/l in a cyclic ether solvent and
precipitating the resulting catalyst of Formula 1 from said reaction mixture during the reaction.

In a specific embodiment of the method, the resulting ruthenium-indenylidene catalyst of Formula 1 may precipitate in a crystalline cyclic ether solvate.

Preferably, it may precipitate as a crystalline cyclic ether solvate comprising >1 cyclic ether molecules per molecule of catalyst According to the method of the present invention, the starting complex (PPh$_3$)$_2$Cl$_2$Ru(3-phenylindenylidene) is present in a mixture or solution with a cyclic ether solvent having a concentration in the range of c=0.2 to 0.6 mol catalyst/l, preferably in the range of c=0.2 to 0.5 mol Ru-catalyst/l.

The cyclic ether solvent generally is selected from the group consisting of tetrahydrofurane (THF), methyl-tetrahydrofuran, dimethyltetrahydrofuran and mixtures or combinations thereof.

In a preferred embodiment, the cyclic ether solvent is tetrahydrofurane (THF). In this preferred embodiment, the resulting ruthenium catalyst of Formula 1 is precipitated from the reaction mixture in crystalline form as a tetrahydrofurane (THF) solvate comprising between 1 and 2 molecules of THF per molecule of catalyst. The molecular formula of this M1 catalyst product may then be given as C$_{51}$H$_{76}$Cl$_2$P$_2$Ru×n (C$_4$H$_8$O) wherein 1≤n≤2.

Typically, the tricyclohexylphosphine (PCy$_3$) ligand is added to the reaction mixture in quantities in the range of 2 to 3 equivalents, preferably 2.1 to 2.5 equivalents based on the (PPh$_3$)$_2$Cl$_2$Ru(3-phenylindenylidene) starting complex.

The reaction temperature conditions are typically under solvent reflux, thus the boiling point of the cyclic ether solvent is decisive here. Generally the reaction temperature should be in the range of 30 to 100° C. When using THF, the reaction temperature should be in the range of 50 to 80° C. (i.e. within the boiling range of THF).

Optionally, the method may further comprise a cooling-down step. To facilitate product precipitation, the reaction mixture may be cooled down to room temperature and below, i.e. to a temperature in the range of −30 to 25° C., preferably to a temperature in the range of 0 to 25° C.

Suitable reaction times are depending on the reaction scale and should be in the range of 0.1 to 3 hours, preferably in the range of 0.5 to 2 hours.

In order to increase the product yield, the cyclic ether solvent may be partially distilled off during the reaction, either under vacuum or under a flow of inert gas.

In a further embodiment, the method comprises steps and measures of separating the catalyst product from the reaction mixture. Such isolation may be performed by filtration, centrifugation, decantation or other similar operations known to the skilled person.

In still further embodiments, the method may comprise additional washing and/or drying steps. Preferably, ketone solvents, such as methylethyl ketone or acetone are preferably employed for washing. Drying of the catalyst may be performed in box ovens under inert atmosphere or under vacuum conditions at elevated temperatures.

In a further aspect, the present invention is directed to a new crystalline form of the Umicore M1 catalyst.

It has surprisingly been found that by working under the specific concentrated conditions, the M1 product precipitates from the reaction mixture as a crystalline material (i.e. in dark red crystals) during the reaction. Experimental data prove that the M1 catalyst product obtained according to the method of the present invention crystallizes with THF solvent molecules in the crystal lattice.

FIG. 1 shows the ORTEP plot of the single-crystal structure of M1 catalyst (THF-solvate) as determined by X-ray analysis. The crystallized complex comprises two co-crystallized THF molecules. The ellipsoids probability is shown at 50%, H-atoms are omitted. Space group is orthorhombic (Pca2(1)). Cell dimensions and angles: a=20.520(4), b=14.543(3), c=18.761(5); α=90.00°, β=90.00°, γ=90.00°. The product crystallizes in dark red crystals.

A beneficial effect of the product crystallinity of the present invention is the ease with which the crystalline M1 material can be handled, filtered and washed. Product washing is necessary to remove $PPh_3$ and other impurities generated in the reaction.

It has been found that the crystalline M1 product may loose some THF during washing, drying and further handling. However, the crystalline product obtainable by the method of the present invention comprises >1 molecule of cyclic ether per molecule of catalyst (as determined by X-ray analysis and $^1$H-NMR spectroscopy). Preferably, the crystalline M1 product comprises between 1 and 2 molecules of THF per molecule of catalyst (as determined by X-ray analysis and $^1$H-NMR spectroscopy).

The orange catalyst product which is state of the art (ref to the earlier cited preparation methods) comprises very fine needles. The orange form of the catalyst material produced according to standard methods is very bulky. In this form, the material is very difficult to filtrate, wash and to handle. The filtration time of the orange version is substantially prolonged, which in turn results in a product of low purity. It is likely that upon precipitation, the impurities are trapped in the orange version due to its flocculent form. The orange catalyst material is also more sensitive to the air oxygen since it has a larger specific surface area. As a consequence, it is much easier oxidized and it likely contains more phosphine oxides impurities unless it is rigorously stored under inert conditions.

According to the known procedures in the art, the desired bis-$PCy_3$ complex may be obtained in acceptable purity only by using a large excess of $PCy_3$ (typically in the range of 3 equivalents) which is not feasible from an industrial point of view due to the high cost of $PCy_3$. Alternatively, the mixture of complexes is isolated and subjected to further treatment with $PCy_3$. This is again not feasible at industrial scale because additional purification steps are needed.

The inventors have further observed that the known synthesis route A, which is the basis of the method of the present invention, basically yields a product which may contain variable amounts of the side product X (=Ru complex with mixed substituents comprising a $PCy_3$ and a $PPh_3$ ligand) according to the following equation 3:

Equation 3:

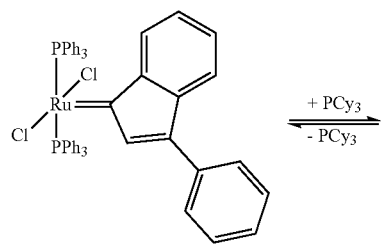

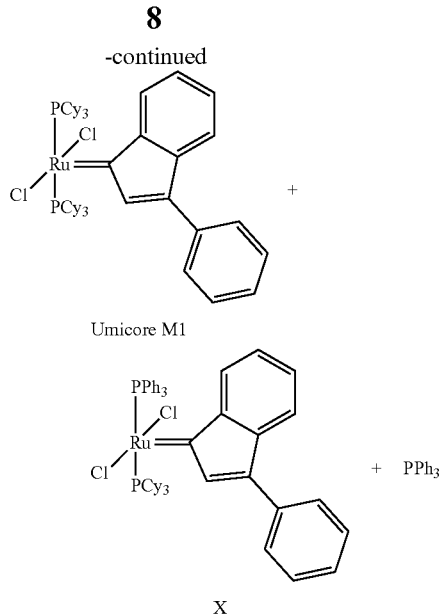

Umicore M1

X

Since the ligand exchange reaction is an equilibrium reaction, the skilled person would expect that a much less cleaner product would be obtained by working under high concentrations: as the reaction proceeds, the amount of $PCy_3$ diminishes while the amount of liberated $PPh_3$ grows; this leads to a mixture of starting material, product M1 and mixed complex X.

To the contrary, the inventors surprisingly found that when working with high concentrations in the range of c=0.2 to 0.6 mol catalyst/l, the product precipitates simultaneously from the reaction mixture so that it is removed from the reaction equilibrium, which is then shifted to the right side, thus affording the desired catalyst product M1 in very good yields and exceptional quality.

The catalyst produced according to the method of the invention is a crystalline material which shows high purity. The high purity is a direct consequence of the crystalline shape of the product.

Typically, the amount of impurity X in the M1 product made according to the invention is <3%, preferably <1% and most preferred <0.5% (based on the total weight of the catalyst product). The presence of mixed complex X in M1 will deteriorate its catalytic activity since it is known that the Ru-indenylidene complex bearing $PPh_3$ groups is not metathesis active. This impurity X can be easily identified by $^{31}$P-NMR as it displays two small peaks close to the product peak (when measured in $CD_2Cl_2$) or only one small peak (when measured in $CDCl_3$).

For quantitative determination of purity, the peak integration method is employed. Based on the impurity data given above, the purity of the Ru-indenylidene catalyst prepared according to the invention is >97%, preferably >99% and particularly preferred >99.5% (as determined by $^{31}$P-NMR spectroscopy).

FIGS. 2a-c, show the XRD diffractograms of three batches of catalyst Umicore M1 made according to the method of the present invention, which, according to $^1$H-NMR analysis, contain different amounts of THF per mol Ru complex respectively:

FIG. 2a shows a XRD plot of M1 (red crystalline material, method of this invention, containing 1.54 mol THF per mol of complex), FIG. 2b shows a XRD plot of M1 (red crystalline material, method of this invention, containing 1.4 mol THF per mol of complex), FIG. 2c shows a XRD spectrum of M1 (red crystalline material, method of this invention, containing 1.1 mol THF per mol of complex).

The detailed conditions for XRD measurements are given in the Examples section.

In general, the intensities of the peaks and the position of the peaks at various diffraction angles (2θ°) may slightly vary depending on the sample preparation, on the measurement conditions as well as on the THF content. The uncertainty in the peak position is +/−0.05° 2θ.

Figure 1:
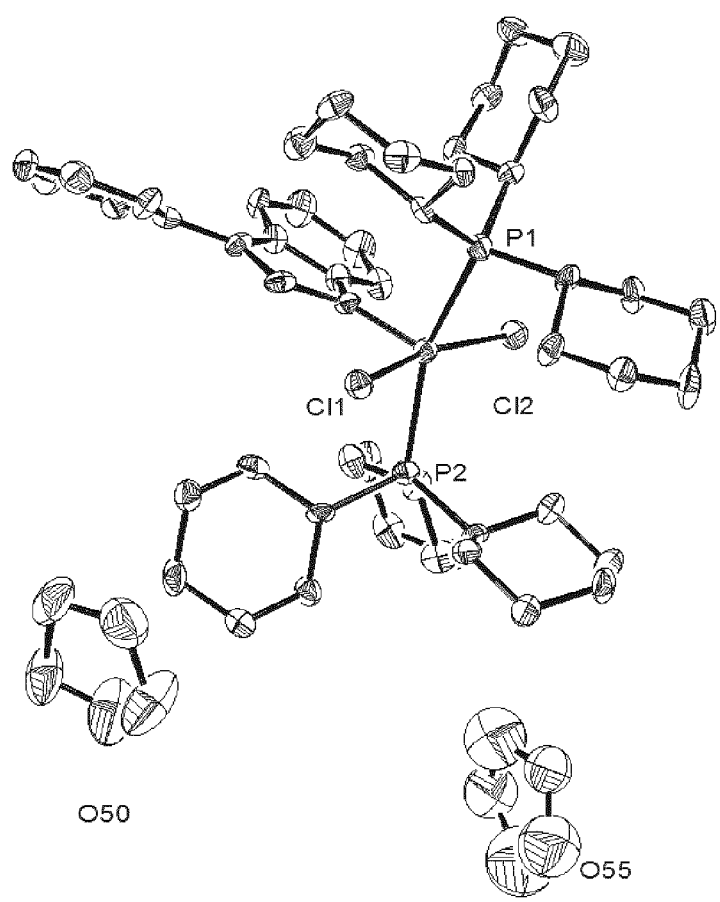
Figure 2A:
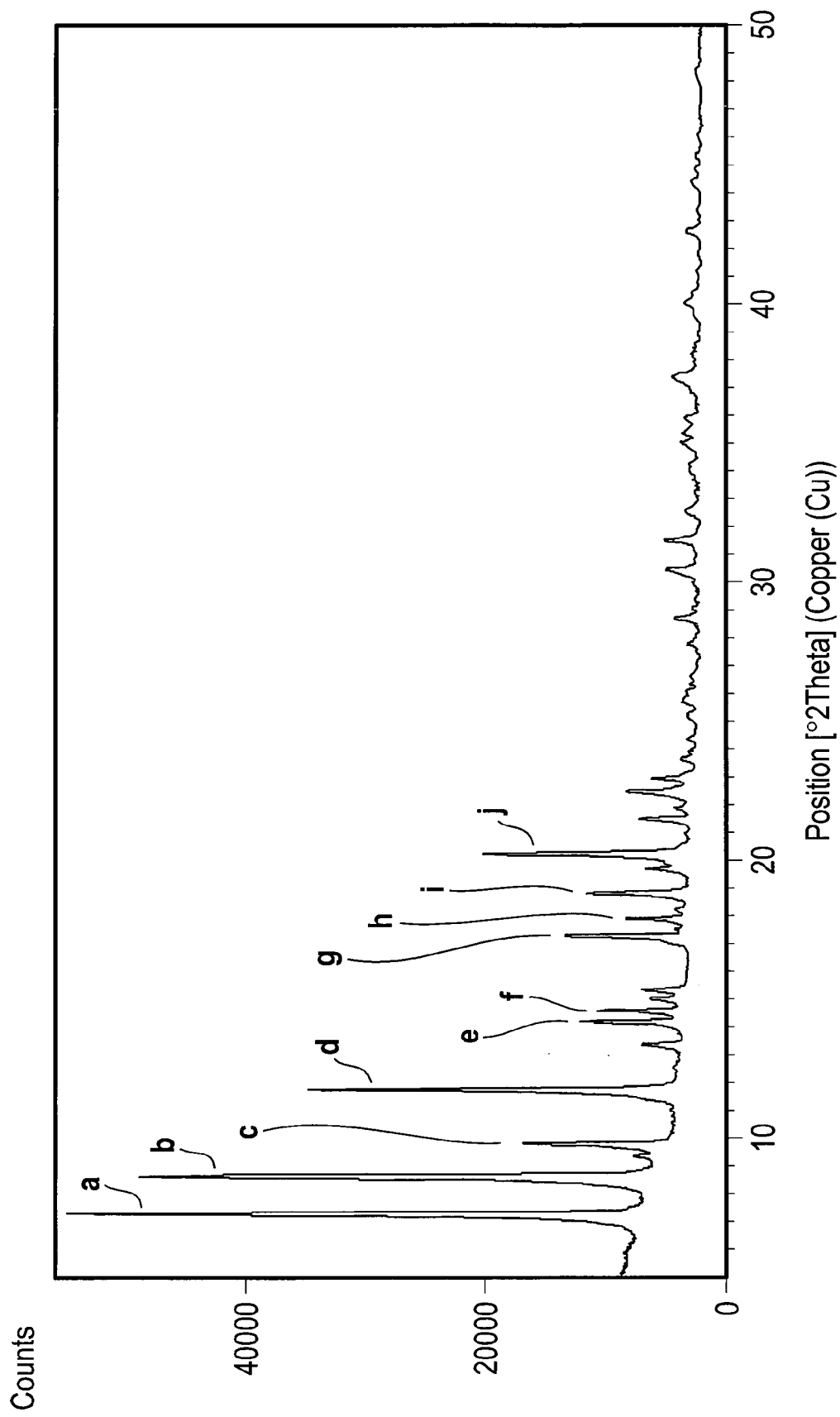
Figure 2B:
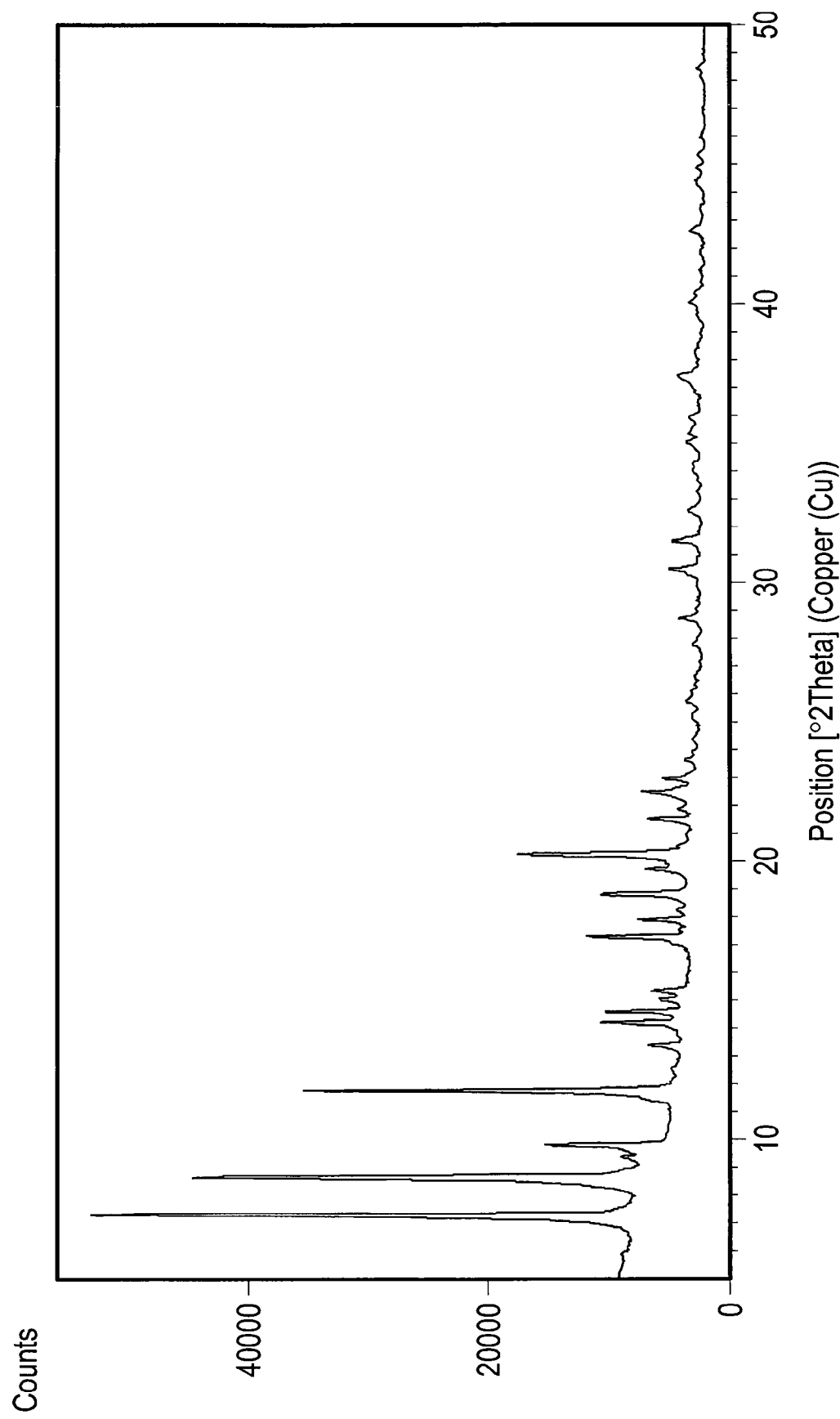
Figure 2C:
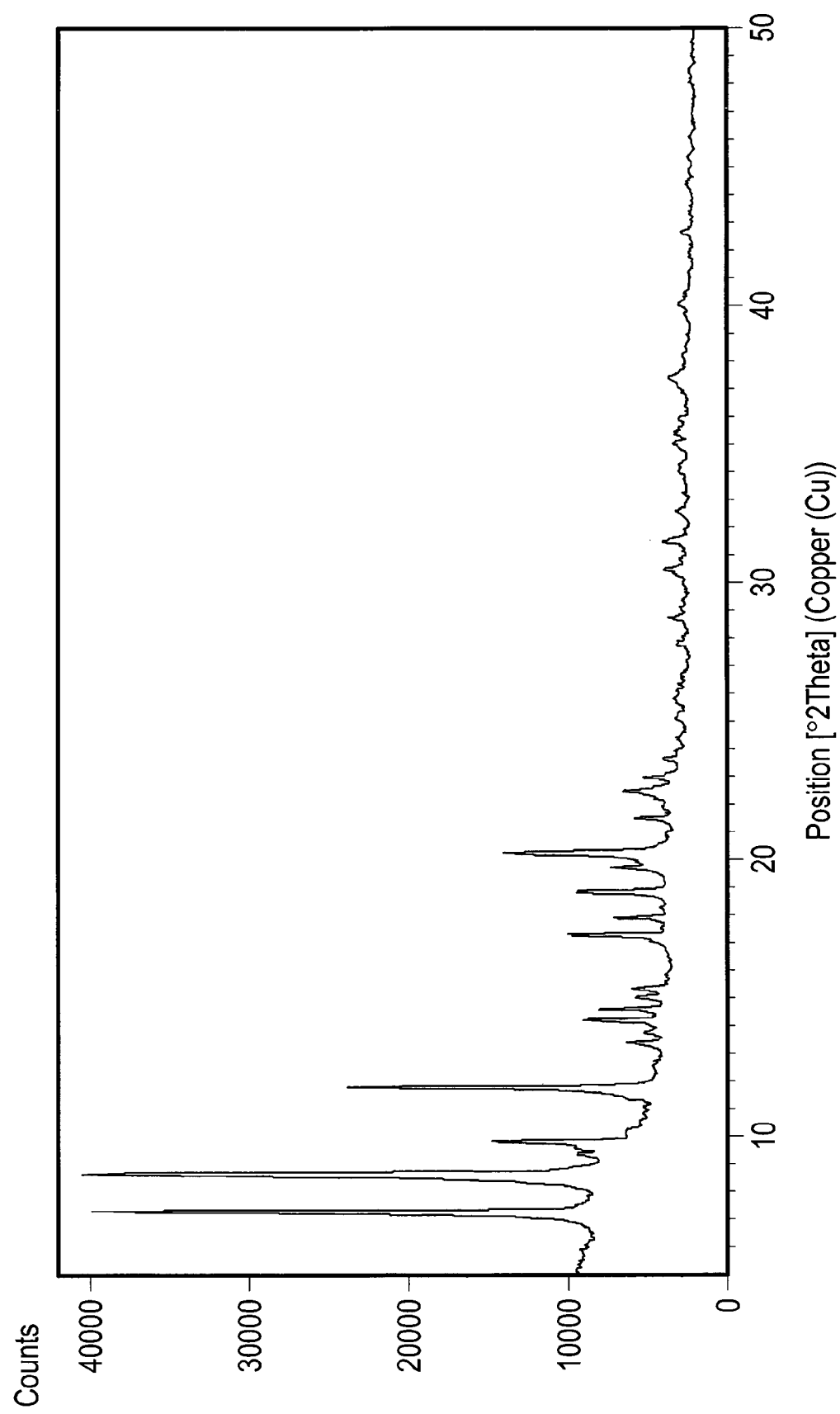
Figure 3A:
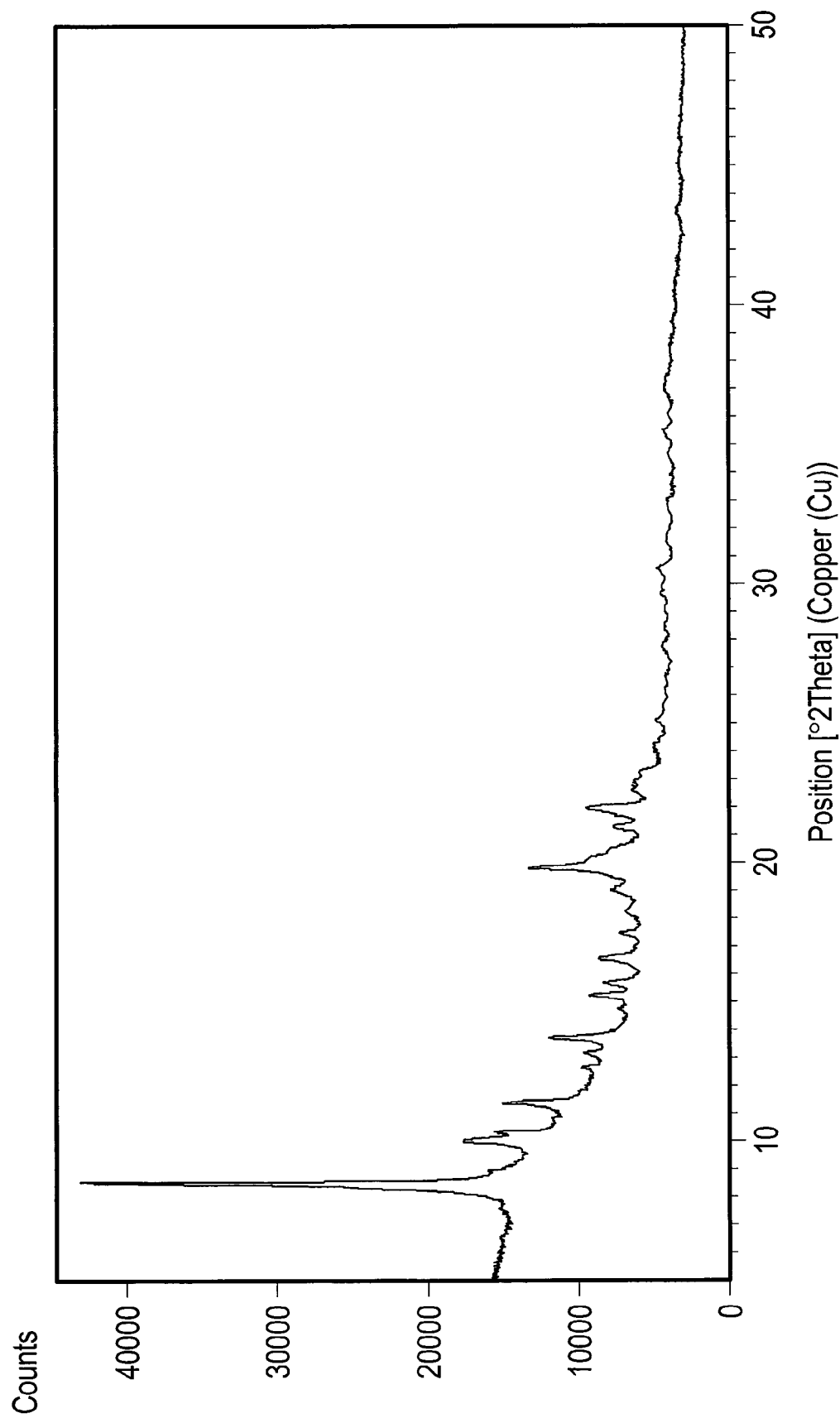
FIG. 3a shows for comparative reasons a XRD diffractogram of the M1 catalyst made according to Umicore Standard Method (acc to WO2010/037550A1), which does not contain any THF (as confirmed by $^1$H NMR). This product exhibited a bulk density of 0.3 g/ml.
Figure 3B:
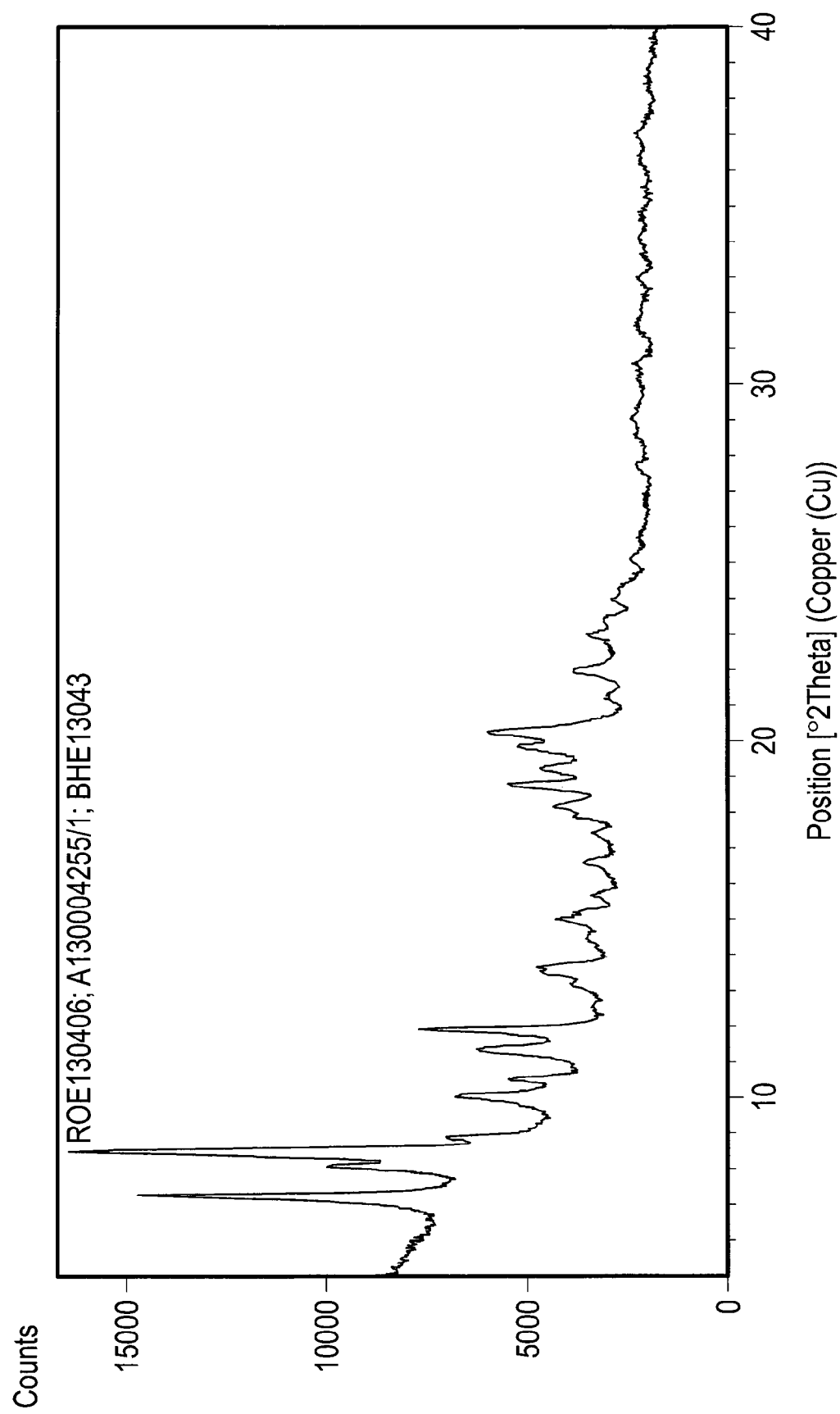
FIG. 3b shows for comparative reasons a XRD diffractogram of the M1 catalyst made according to EP 2280033, Example 9, which contains less than 0.1 mol THF/mol product (as confirmed by $^1$H NMR). This product exhibited a bulk density of 0.25 g/ml.

As a summary, from the analysis of the XRD diffractograms shown in FIGS. 2a-d vis-a-vis 3a and 3b, it is clearly evident that the M1 product made according to the method of the present invention displays a higher crystallinity and furthermore has a different constitution compared to the material available according to the prior art. The Umicore M1 obtained by the method of the present invention reveals characteristic peaks at various diffraction angles (2θ° values) as listed in Table 1. In this table, relative peak intensities are also listed. Moreover, it can be seen from the amorphous halo of the diffractograms in FIGS. 3a and 3b that the cristallinity of these compounds according to the prior art is lower than the cristallinity of the compounds obtained according to the subject patent application. Furthermore, the reflexes in 3a and 3b and their pattern are different from FIGS. 2a-d.

In addition, a powder diffractogram was simulated (software X'Pert HighScore Plus of PANalytical) based on the crystal data of the single crystal analysis of the THF-solvate. It has been found that the simulated diffractogram is directly comparable to that one obtained experimentally with the material produced according to the present invention. The simulation confirms that Umicore M1 made according to the method of the present invention contains THF molecules in the crystal.

TABLE 1

Peak analysis of XRD diffractogram of Umicore M1 catalyst (made according to the method of the invention)

| Peak No. | diffraction angle (2θ°) | rel. intensity*) |
|---|---|---|
| a | about 7.3 | s |
| b | about 8.7 | s |
| c | about 9.8 | m |
| d | about 11.8 | s |
| e | about 14.2 | m |
| f | about 14.6 | m |
| g | about 17.3 | m |
| h | about 17.9 | w |
| i | about 18.8 | m |
| j | about 20.3 | m |

*)relative peak intensities: s = strong; m = medium; w = weak

In FIG. 4, SEM pictures of two different batches of catalyst Umicore M1 are shown.

Figure 4A:

FIG. 4a shows M1 (red crystalline material, THF solvate, method of this invention).

Figure 4B:
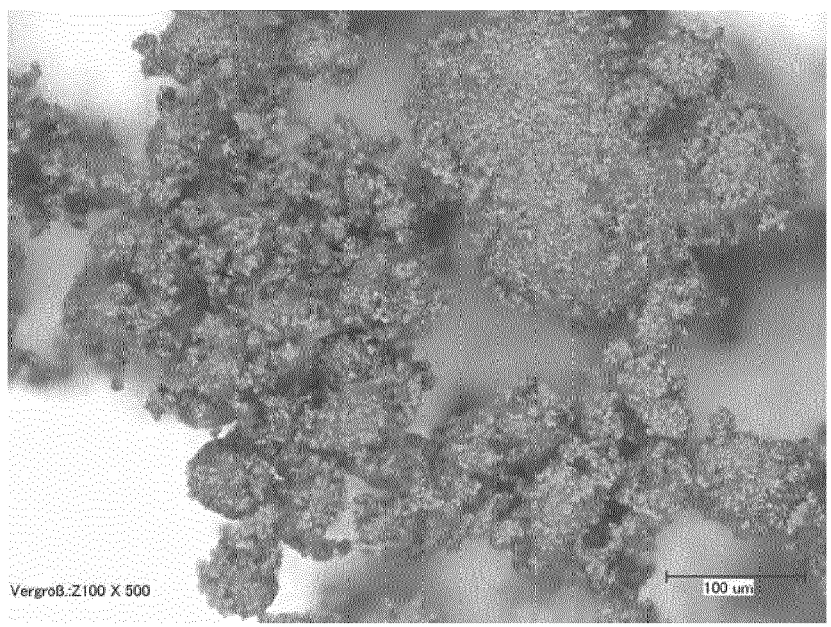

FIG. 4b shows M1 (orange material, Umicore Standard method).

By these figure, the highly crystalline nature of the catalyst M1 made according to the method of the present invention is clearly demonstrated.

In summary, due to the preparation method of the present invention, the resulting Ru-indenylidene catalyst M1 reveals high product purity, in particular high crystallinity. As easily scaleable precipitation processes are employed, this preparation method is applicable to industrial production scale.

The Umicore M1 catalyst of the present invention is useful in a variety of olefin metathesis reactions such as ring-closing metathesis (RCM), ring-opening metathesis polymerization (ROMP) and cross metathesis (CM). Furthermore, it is a valuable precursor for the synthesis of other, further modified ruthenium carbene catalysts.

The present invention is directed to a method for the preparation of ruthenium catalyst $(PCy_3)_2Cl_2Ru(phenylindenylidene)$ (Umicore catalyst "M1"). The method comprises a one-step reaction reacting the precursor compound $(PPh_3)_2Cl_2Ru(3$-phenylindenylidene) with $PCy_3$ in a cyclic ether solvent (preferably THF) in concentrations in the range of 0.2 to 0.6 mol catalyst/l while simultaneously precipitating the product from the reaction mixture. A cyclic ether solvate product with high crystallinity and high purity is obtained.

The present invention is further directed to a crystalline modification of ruthenium catalyst Umicore M1 $(PCy_3)_2Cl_2Ru(phenylindenylidene)$ comprising between 1 and 2 molecules of THF per molecule of catalyst and having the molecular formula $C_{51}H_{76}Cl_2P_2Ru \times n(C_4H_8O)$ wherein $1 \leq n \leq 2$.

The invention is further described in the following examples without restricting its scope of protection.

EXAMPLES

Generally, in the Examples glass reactors or flasks with condenser and stirrer are used for the method of the present invention. The reactors are flushed with dry inert gas (argon, nitrogen) prior to use.

The NMR spectra are recorded on a BRUKER DRX 500 NMR spectrometer at about 25° C. The chemical shifts are determined relative to external phosphoric acid ($^{31}$P-NMR) or to residual solvent signal ($^1$H-NMR).

The XRD diffractograms were recorded in the range 5°<2θ<100° on a PANalytical X'Pert Pro with X-Celerator detector using Cu radiation. The sample material was prepared into a 27 mm PAN analytical sample holder (single preparation).

The XRD data were recorded under the following conditions:

| Instrument | PANalytical X'Pert Pro |
|---|---|
| X-ray tube | LFF-Cu-X-ray tube |
| K-beta Filter | Nickel |
| Detector | X'Celerator |
| x-ray tube excitation | 40 kV, 40 mA |
| Divergence slit | fixed |
| Divergence slit size | ½° |
| Anti-scatter slit | 1° |
| 2-Theta range | 5° to 100° |

| | |
|---|---|
| Measurement Mode | Continuous |
| Time per step | 40 s |
| Step size | 0.017° (2 Theta) |
| Rotation | 1 Rev/s |

The uncertainty in the peak position is +/−0.05° 2θ.

Example 1

Preparation of Starting Complex $(PPh_3)_2Cl_2Ru(3$-phenylindenylidene) According to Prior Art (Ref to H.-J. Schanz et al., Cited Above)

A one liter glass reactor with condenser and stirrer is filled with argon and thereafter with 800 ml of THF. The solvent is warmed up to 50° C. Then 19.7 g (98.6% purity, 93.2 mmol, 1.15 eq.) of 1,1-diphenyl-2-propyn-1-ol, 2.91 ml (40.5 mmol, 0.5 eq.; GFS Chemicals Inc., Powell, Ohio, USA) of acetylchloride and 99.6 g (81 mmol, 1 eq.) of $Ru(PPh_3)_{3-4}Cl_2$ (Ru-content 8.22 wt. %; Umicore AG & Co. KG, Hanau) are added successively during stirring. The reaction mixture is stirred under reflux (65° C.) for 90 min. Then it is cooled down to 50° C. and 700 ml of THF solvent are distilled off under vacuum. The red-brown suspension is cooled down to room temperature and isopropanol (600 ml) is added under stirring. The resulting precipitate is filtered off, washed with isopropanol and petroleum ether and then dried under vacuum at 40° C.

Yield: 85% (based on Ru-content).

$^{31}$P-NMR $(C_6D_6)$: δ=27.8 ppm (s)

Example 2

Preparation of dichloro(3-phenyl-1H-inden-1-ylidene)bis-(tricyclohexylphosphine)ruthenium(II) (According to the Invention; c=0.5 mol/l)

Equation IV:

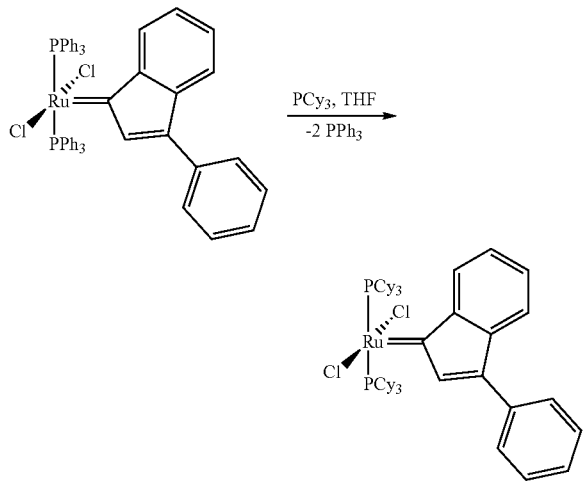

A one liter glass reactor with condenser and stirrer is filled with argon and thereafter with 500 ml of THF. The solvent is warmed up to 40° C. Then 221.7 g (250 mmol, 1 eq.) of $(PPh_3)_2Cl_2Ru(3$-phenylindenylidene) (Umicore AG & Co. KG, Hanau) and 155 g (98.1% purity, 540 mmol, 2.16 eq.) of tricyclohexylphosphine ($PCy_3$, Aldrich) are added successively with stirring. The reaction mixture is stirred under reflux (65° C.) for 1 h during which time the product precipitates in form of dark red crystals. The reaction mixture is cooled down to 5° C. The crystalline precipitate is filtered off, washed with 400 ml of acetone and then dried under vacuum at 80° C. Yield: 236 g, 88% (based on Ru-content 9.41 wt.-%).

$^{31}$P-NMR $(CD_2Cl_2)$: (ppm)=32.0 (s, product), 31.28 and 31.18 (side product). Purity based on $^{31}$P-NMR: >99%.

$^1$H-NMR $(CD_2Cl_2)$: δ (ppm)=8.66 (d, product, 1H), 7.96 (d, side product, <0.01H), 7.75 (m, product, 2H), 7.7 (m, side product, <0.02H), 7.52 (m, product, 1H), 7.40 (ms, product, 3H), 7.28 (m, product, 2H), 7.05 (td, side product, <0.01H), 7.016 (s, side product, <0.01H), 3.68 (m, THF, 6.4H), 2.60 (m, product, 6H), 1.9-1 (ms, product, 27H), 1.82 (m, THF, 6.4H). Other signals of the side product are covered by the signals of the product. THF-content based on $^1$H-NMR=1.6 mol THF/mol product (~11 wt.-%). Side-product content based on $^1$H-NMR=<0.01 mol (<1 wt.-%).

Bulk density: 0.45 g/ml

Space yield: 236 g/l

Example 3

Preparation of dichloro(3-phenyl-1H-inden-1-ylidene)-bis-(tricyclohexylphosphine)ruthenium(II) (According to the Invention; c=0.2 mol/l)

A one liter glass reactor with condenser and stirrer is filled with argon and thereafter with 600 ml of THF. Then 106.4 g (120 mmol, 1 eq.) of $(PPh_3)_2Cl_2Ru(3$-phenylindenylidene) (Umicore AG & Co. KG, Hanau) and 74 g (98.1% purity, 258 mmol, 2.15 eq.) of tricyclohexylphosphine, $PCy_3$ are added successively with stirring. The reaction mixture is stirred under reflux (65° C.) for 0.5 hour. Then it is cooled down to 40° C. and 250 ml of THF solvent are distilled off causing the precipitation of the product in form of dark red crystals. Alternatively the solvent may be removed by a stream of inert gas during the reaction. The resulting red suspension is cooled down to 5° C. and acetone (500 ml) is added under stirring. The crystalline precipitate is filtered off, washed with acetone and then dried under vacuum at 80° C. Yield: 108 g, 85% (based on Ru-content, 9.54 wt.-%).

Purity ($^{31}$P-NMR): >99%. The analytical data of the product are comparable to those of Example 2.

Space yield: 108 g/l

Comparative Example 4

Preparation of dichloro(3-phenyl-1H-inden-1-ylidene)-bis-(tricyclohexylphosphine)ruthenium(II) (According to EP 2280033, Example 9)

A 500 ml Schlenk flask was purged with argon for 15 minutes. 5.21 mmol (5.0 g) $RuCl_2(PPh_3)_3$ and 8.49 mmol (1.79 g) 1,1-diphenyl-2-propin-1-ol were placed into the flask. 267 ml absolute tetrahydrofurane were added and the reaction mixture was stirred at reflux for 3 hours. The mixture was evaporated by 50% in vacuum and 16.67 mmol (4.76 g) tricyclohexylphosphine were added. The suspension was stirred for 8 hours at room temperature under argon. Then the solvent was removed in vacuum. The oily residue was added with 135 ml of acetone. The mixture was stored for 10 hours at −20° C. The residue was filtered by suction filtration (nutsche filter, porosity D4). The solid was washed with methanol, acetone and hexane. The product was dried in vacuum at room temperature. The product was obtained as brick-red powder, 4.63 g (5.02 mmol, 87% yield on metal base).

Analysis
Bulk density: 0.25 g/ml
Space yield: about 14 g/L
Purity ($^{31}$P NMR): about 80%.
THF-content (based on $^1$H NMR, $CD_2Cl_2$, 20° C.): <0.1 mol THF/mol product (<0.5 wt.-%).

$^{31}$P and $^1$H-NMR data shows the presence of several side products: diphenylallenylidene complex (δ≈41 ppm in $^{31}$P NMR) and phosphine oxides.

The invention claimed is:

1. A method for preparation of the ruthenium-indenylidene carbene catalyst of Formula 1,

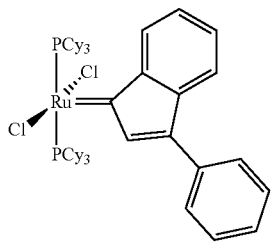

Formula 1 said method comprising
reacting $(PPh_3)_2Cl_2Ru$(3-phenylindenylidene) with tricyclohexyl-phosphine ($PCy_3$) in a reaction mixture having a concentration in the range of 0.2 to 0.6 mol Ru-catalyst/l in tetrahydrofurane (THF) as a solvent and
precipitating the resulting catalyst of Formula 1 during the reaction.

2. The method according to claim 1, wherein the catalyst of Formula 1 precipitates in the form of a crystalline tetrahydrofurane (THF) solvate.

3. The method according to claim 2, wherein the tetrahydrofurane (THF) solvate comprises >1 molecule of THF per molecule of catalyst.

4. The method according to claim 1, wherein the reaction temperature is in the range of 30 to 100° C.

5. The method according to claim 1, wherein the $PCy_3$ is present in the range of 2 to 3 equivalents.

6. The method according to claim 1, wherein the solvent tetrahydrofuran (THF) may be partially distilled off during the reaction.

7. The method according to claim 1, further comprising a cooling step, wherein the reaction mixture is cooled down to a temperature in the range of −30 to 25° C.

8. The method according to claim 1, wherein the reaction time is in the range of 0.1 to 3 hours.

9. The method according to claim 1, further comprising steps of separating the resulting ruthenium-indenylidene catalyst from the reaction mixture.

10. The method according to claim 1, further comprising steps for washing and drying the resulting ruthenium-indenylidene catalyst.

* * * * *